US009028847B2

(12) United States Patent
Li et al.

(10) Patent No.: US 9,028,847 B2
(45) Date of Patent: May 12, 2015

(54) SODIUM ALGINATE CROSSLINKED SLOW-RELEASE MOXIFLOXACIN MICROSPHERE, THE PREPARATION METHOD AND THE USE THEREOF, AND TARGET VASCULAR OCCLUSIVE AGENT OF THE MICROSPHERE

(75) Inventors: Xinjian Li, Beijing (CN); Hong Hong, Beijing (CN)

(73) Assignee: Beijing Shengyiyao Technology & Development Co., Ltd., Beijing (CN)

( * ) Notice: Subject to any disclaimer, the term of this patent is extended or adjusted under 35 U.S.C. 154(b) by 0 days.

(21) Appl. No.: 13/809,361

(22) PCT Filed: Dec. 30, 2010

(86) PCT No.: PCT/CN2010/080549

§ 371 (c)(1),
(2), (4) Date: Feb. 22, 2013

(87) PCT Pub. No.: WO2012/003704

PCT Pub. Date: Jan. 12, 2012

(65) Prior Publication Data

US 2013/0156827 A1 Jun. 20, 2013

(30) Foreign Application Priority Data

Jul. 9, 2010 (CN) .......................... 2010 1 0222446

(51) Int. Cl.

*A61K 9/16* (2006.01)
*A61K 31/4709* (2006.01)
*C07D 471/04* (2006.01)

(52) U.S. Cl.

CPC ............ *A61K 9/1658* (2013.01); *C07D 471/04* (2013.01); *A61K 9/16* (2013.01); *A61K 31/4709* (2013.01); *A61K 9/1682* (2013.01); *A61K 9/1652* (2013.01)

(58) Field of Classification Search

USPC .......................................... 424/400; 514/300
See application file for complete search history.

(56) References Cited

U.S. PATENT DOCUMENTS

| | | | | |
|---|---|---|---|---|
| 1,051,520 | A * | 1/1913 | Schindler | 514/504 |
| 2009/0054501 | A1* | 2/2009 | Boechat et al. | 514/359 |
| 2009/0162440 | A1* | 6/2009 | Xiaoping et al. | 424/489 |
| 2010/0247666 | A1* | 9/2010 | MacLeod et al. | 424/501 |

FOREIGN PATENT DOCUMENTS

| | | | |
|---|---|---|---|
| CN | 1850035 | A | 10/2006 |
| CN | 1879607 | A | 12/2006 |
| CN | 101254169 | A | 9/2008 |
| WO | WO 2007008752 | A2 * | 1/2007 |
| WO | WO 2008059223 | A2 * | 5/2008 |
| WO | WO 2009089147 | A2 * | 7/2009 |

OTHER PUBLICATIONS

English Abstract of CN 1850035 A (1 page).
English Abstract of CN 101254169 A (1 page).
English Translation of claims 10-12 and examples of the description of CN 1879607 A (3 pages).
International Search Report of corresponding Application No. PCT/CN2010/080549, dated Apr. 21, 2011, with English Translation (6 pages).

* cited by examiner

*Primary Examiner* — Rachael E Bredefeld
*Assistant Examiner* — Dominic Lazaro
(74) *Attorney, Agent, or Firm* — Christie, Parker & Hale, LLP

(57) ABSTRACT

A sodium alginate crosslinked slow-released moxifloxacin microsphere, the preparation method of the microsphere, a vascular target embolus containing the microsphere and the use of the microsphere in preparing the vascular target embolus. The microsphere contains moxifloxacin, a drug carrier, a adsorbent, a reinforcing agent and a solidifying agent, wherein the drug carrier is sodium alginate, the adsorbent is albumin prepared from human plasma or bovine serum albumin, the reinforcing agent is gelatin or hyaluronic acid, and the solidifying agent is a divalent metal cation chosen from calcium salt or barium salt.

20 Claims, No Drawings

SODIUM ALGINATE CROSSLINKED SLOW-RELEASE MOXIFLOXACIN MICROSPHERE, THE PREPARATION METHOD AND THE USE THEREOF, AND TARGET VASCULAR OCCLUSIVE AGENT OF THE MICROSPHERE

CROSS REFERENCE TO A RELATED APPLICATION (S)

This application is a National Phase Patents Applications and claims priority to and benefit of International Application Number PCT/CN2010/080549, filed on Dec. 30,2010, which claims priority to and benefit of Chinese Patent Application Number 201010222446.0, filed on Jul. 9,2010, the entire disclosure of which are incorporated herein by reference.

TECHNICAL FIELD

The present invention relates to a microsphere containing an anti-tuberculosis drug and a vascular targeted embolic agent comprising the microsphere, particularly relates to a sustained-release microsphere with moxifloxacin as an anti-tuberculosis active ingredient and sodium alginate as a carrier for crosslinking and vascular targeted embolic agent thereof. The present invention also relates to a method for preparing the sustained-release microsphere, and use of the microsphere in preparing drugs for treating pulmonary tuberculosis, mass hemoptysis of pulmonary tuberculosis, pulmonary tuberculosis cavity, renal tuberculosis, thyroid tuberculosis, cervical lymph node tuberculosis, genital tuberculosis (fallopian tube tuberculosis, endometrium tuberculosis, testis tuberculosis, epididymis tuberculosis), pericardial tuberculosis, chest wall tuberculosis, pleural tuberculosis and other tuberculosises in the body through interventional embolization.

BACKGROUND TECHNOLOGIES

Tuberculosis is one of major infectious diseases seriously harming human life and health, and also becomes the number-one killer in infectious diseases and the leading cause of death for adults. In the late 1990s, due to drug-resistant bacteria and other issues, the tuberculosis which had disappeared made a comeback throughout the world, which increased difficulties in controlling the tuberculosis. The World Health Organization has made preliminary statistics showing that 1.9 billion people around the world are infected by tuberculosis bacilli, the number of patients with tuberculosis has been up to about 20 million, the number of new cases is up to 8 million each year, and 3 million people on average die from tuberculosis each year. In China, the number of patients infected by tuberculosis bacilli are also rising, and tuberculosis presents an upward trend, the number of patients with tuberculosis ranks the second in the world, and the number of deaths due to tuberculosis each year is about 150,000; prevention and treatment of tuberculosis is a major issue that needs to be resolved urgently, and therefore research and development of new anti-tuberculosis drugs and new dosage forms is imminent.

*Mycobacterium tuberculosis* mainly parasitizes in normal cells and has some resistance to drugs, and *Mycobacterium tuberculosis* can be killed only when concentration of an anti-tuberculosis drug in the cell reaches a certain level. Oral formulations of anti-tuberculosis drugs are often influenced by the first-pass effect firstly, and subjected to protein binding, metabolism, excretion, decomposition and other processes during circulating around the body, but only a small amount of drug can reach the target tissue, target organ and target cell, therefore, in order to improve concentration of the drug in the target area, dose of the drug must be increased, which enhances systemic toxic and side effects of the drug. Targeted formulations have characteristics such as directionally releasing drugs, increasing concentration of drugs in lesion sites and cells, improving efficacy, reducing toxic and side effects, therefore it is considered that the anti-tuberculosis drug targeted formulations have clinical application value and development prospects.

Moxifloxacin, which belongs to the fourth-generation chemically synthesized antibiotic drugs of fluoroquinolones, is a product launched by Bayer (Germany) in 1999. Moxifloxacin blocks replication of DNA by inhibiting activities of bacterial DNA gyrase A subunit and topoisomerase IV to play roles in killing bacteria. For gram-negative bacteria, moxifloxacin mainly inhibits the DNA gyrase, and for gram-positive bacteria, the primary action target is the topoisomerase IV. Chemical structure of moxifloxacin is characterized in that the methoxyl is introduced to the $8^{th}$ carbon atom, which increases the drug's capability of binding to the bacteria and capability of penetrating and destroying the cell membrane, and its post-antibiotic effect (PAE) is strong and lasting.

Moxifloxacin retains antibacterial activity and antibacterial spectrum of quinolone drugs on gram-negative bacteria, and the methoxyl at the $8^{th}$ carbon atom increases antibacterial activity and broadens antibacterial spectrum of moxifloxacin on gram-positive bacteria. Moxifloxacin is extremely effective to atypical pathogens such as mycoplasma pneumoniae, chlamydia, and legionella, and has strong activity on anaerobic bacteria, for example, it has significant antibacterial activity on anaerobic bacteria with or without spores. Moxifloxacin is also effective to bacteria which are resistant to antibiotics of β-lactams, macrolides, amino glycopeptides and tetracyclines. Moxifloxacin, different from the hepatic cytochrome P-450 isozyme inhibitor, has no drug cross-resistance with these antibiotic drugs, thus avoiding many potential interactions between drugs. Moxifloxacin has similar early bactericidal activity to isoniazid (INH) or rifampin, and has bactericidal activity for early and extended early stage of patients with pulmonary tuberculosis, which shows that moxifloxacin can well penetrate into the tuberculosis lesion sites and quickly kill the fast growing flora in the sputum of patients with severe cavitary pulmonary tuberculosis.

Since it is on the market, moxifloxacin has been widely applied clinically due to its advantages such as broad antibacterial spectrum, strong antibacterial power, wide distribution in the body, high drug concentration in the body, long half-life, good efficacy, little side effects, no drug cross-resistance with other antibacterial drugs, almost no photosensitive reactions and the like. With wide application of anti-tuberculosis drugs clinically, drug resistance of *Mycobacterium tuberculosis* gets higher and higher, especially the problem of multi-drug resistance, which has become a subject of concern for the anti-tuberculosis field, and is also a main factor impacting chemotherapy effect on tuberculosis. Therefore, selecting an appropriate dosage form of an anti-tuberculosis drug is important for the current treatment and control of tuberculosis.

Phenomenon of recurrence of tuberculosis and drug resistance of tuberculosis bacilli is becoming more and more serious, despite that there are complex causes for the occurrence of the phenomenon, a very important factor is long treatment course, making patients be unable to take medicine with full amount regularly till the end of treatment, which is a common problem faced in the treatment of tuberculosis in countries of the world. On the premise of ensuing therapeutic effect, the problem of drug compliance can be effectively resolved by reducing dose of a drug and prolonging intervals of administration. In order to obtain an anti-tuberculosis drug formulation which can play a long-lasting effect in human body, we have selected a natural polymer, sodium alginate, with good biocompatibility as a carrier and moxifloxacin as a model drug, to crosslink with an adsorbent, so as to obtain a vascular embolic agent containing sustained-release biodegradable microspheres by prescription selection, release experiments in vitro and studies in vivo.

There are only sporadic reports about study on microspheres carrying an anti-tuberculosis drug at home, most of drugs reported are drugs to be administered orally or by injection. At abroad, systematic study reports about microspheres carrying an anti-tuberculosis drug are mainly concentrated in study groups of America, Japan and India, involving different carriers, different drugs, different microsphere size and different routes of administration. Some scholars were dedicated to study on the anti-tuberculosis sustained-release system before, mainly involving oral agents, inhalants, injections, and subdermal implants.

Currently, clinical anti-tuberculosis drugs are mainly oral and injectable formulations, and the efficacy of the injectable formulation is not ideal. Application of anti-tuberculosis drugs is greatly limited since effective drug concentration cannot be obtained at the lesion site and significant systemic toxicity and drug resistance occur in the application process. A few therapies of embolism plus drug infusion have the following defects: the drug cannot be sustainedly released in a relatively uniform form, and the "shock wave" efficacy of the drug may cause necrosis or damage to local tissues when local drug infusion concentration is too high.

Anti-tuberculosis drug microsphere vascular embolic agent is a new dosage form, wherein microspheres deposit in the lung, which can delay release of the drug, protect the drug from being destroyed by enzyme hydrolysis, and prolong retention time of the drug in the lung, and also has advantages in low incidence rate of side effects, good toleration and safety. At present, there has been no reports at home and abroad about an anti-tuberculosis vascular embolic agent prepared by crosslinking moxifloxacin with sodium alginate and an adsorbent, and about application of the anti-tuberculosis vascular embolic agent in treating patients with pulmonary tuberculosis, mass hemoptysis of pulmonary tuberculosis, pulmonary tuberculosis cavity, bronchial stenosis of pulmonary tuberculosis, multi-drug resistant cavitary pulmonary tuberculosis, renal tuberculosis, thyroid tuberculosis, genital tuberculosis (fallopian tube tuberculosis, endometrium tuberculosis, testis tuberculosis, epididymis tuberculosis), cervical lymph node tuberculosis, pericardial tuberculosis, chest wall tuberculosis, and other tuberculosises of other parts in the whole body through interventional embolization.

Moxifloxacin belongs to the fourth-generation chemical antibiotic drugs of fluoroquinolones, with poor solubility in water and organic solvents. Oral and injectable formulations of moxifloxacin are usually applied clinically and have defects as follows: amount of oral absorption is small, dose of injection is low, an effective drug concentration cannot be obtained at the lesion site, releasing cannot be performed in a relatively uniform and sustained form, and adverse reactions are easily caused.

SUMMARY OF THE INVENTION

The present invention provides a sodium alginate crosslinked moxifloxacin sustained-release microsphere, wherein the microsphere comprises: a drug carrier, adsorbent, anti-tuberculosis drug active ingredient, strengthening agent and curing agent, the carrier is sodium alginate, the adsorbent is human serum albumin or bovine serum albumin, the anti-tuberculosis drug active ingredient is moxifloxacin, the strengthening agent is gelatin or hyaluronic acid, and the curing agent is a salt of divalent metal cation such as divalent calcium or barium salt.

In one embodiment, the sustained-release microsphere is preserved in a vegetable oil or liquid paraffin as a preservation solution, and the particle size of the microsphere is in the range of 50~100 µm, 50~150 µm, 50~200 µm, 100~300 µm, 150~450 µm, 300~500 µm, 500~700 µm, 700~900 µm or 900~1,250 µm.

In another embodiment, the microspheres are made into dry powdered particles with particle size in the range of 10~50 µm, 25~50 µm, 50~100 µm, 100~350 µm, 300~550 µm or 500~750 µm.

In the sustained-release microsphere of the present invention, the weight ratio of sodium alginate and moxifloxacin is preferably 1~75:0.25~12.5.

The present invention also provides a method for preparing the above-mentioned sustained-release microsphere, which comprises the following steps:
1) dissolving sodium alginate with physiological saline or water for injection based on mass-volume percentage of 0.5-15% to obtained a sodium alginate solution, i.e., a carrier solution;
2) dissolving human serum albumin or bovine serum albumin with water for injection based on mass-volume percentage of 0.1-10% to obtain a albumin solution, i.e., an adsorbent;
3) grinding, stirring, dissolving and adsorbing moxifloxacin with the adsorbent prepared in step 2) to obtain a moxifloxacin solution, i.e., a drug solution, wherein moxifloxacin and the adsorbent are added in an amount of mass-volume percentage of 1.6-4%;
4) preparing an aqueous solution of 1-15% by mass-volume with a salt of divalent metal cation such as divalent calcium or barium salt to obtain a curing solution; wherein the calcium salt is preferably selected from calcium chloride and calcium lactate, the barium salt is preferably barium chloride;
5) adding anhydrous ethanol and water for injection into the resulting curing solution, wherein the volume ratio of the resulting curing solution, anhydrous ethanol and water for injection is 2:1:2, so that a curing solution containing anhydrous ethanol is obtained;
6) dissolving gelatin or hyaluronic acid with water for injection to obtain a gelatin or hyaluronic acid solution of 0.1-10% by mass-volume, i.e., a strengthening solution;
7) pooling the drug solution and the carrier solution at a volume ratio of 1:1~30, and magnetically stirring the solution uniformly to obtain a preparing solution;
8) spraying the above-obtained preparing solution by a high voltage electrostatic multi-head microsphere generating device to obtain droplets which are then dispersed in the curing solution, and removing supernatant when precipitation is completed , to obtain sodium alginate crosslinked microspheres or micro-gel beads containing moxifloxacin;
9) adding the above-obtained microspheres or micro-gel beads into the strengthening solution, stirring the solution, and discarding supernatant to obtain microspheres or micro-gel beads containing drug, i.e., sodium alginate crosslinked moxifloxacin sustained-release microspheres.

In one embodiment, the sodium alginate crosslinked moxifloxacin sustained-release microspheres containing drug obtained in step 9) are preserved in vegetable oil or liquid paraffin oil as a preservation solution. The vegetable oil may be selected from soybean oil, tea oil, corn oil, rapeseed oil, cottonseed oil or other oils for injection.

Or, in another embodiment, the sodium alginate crosslinked moxifloxacin sustained-release microspheres are dried to obtain powered particles, i.e., dry spheres, for example, the method of freeze drying or oven drying is employed.

In one special embodiment, the high voltage electrostatic multi-head microsphere generating device used in step 8) comprises: a high voltage electrostatic generating device, propulsion pump, ejecting head, sterile container, a plurality of positive and negative electrodes, sterile syringes of various models, and lifting device, wherein the high voltage electrostatic generating device is provided with the plurality of positive and negative electrodes, the propulsion pump is connected to the sterile syringe and the ejecting head, the positive electrode is connected to the ejecting head, the negative electrode is connected to a stainless steel wire immersed in the curing solution, the stainless steel wire is connected to the sterile container, and the lifting device for adjusting distance is under the stainless steel wire and the sterile container.

When preparing microspheres with the preparing solution, a high electric field is generated between the positive and negative electrodes of every group after the high voltage electrostatic multi-head microsphere generating device is powered on, when the propulsion pump pushes out the mixed solution of sodium alginate and the adsorbed drug at a constant speed, the electric field force overcomes the inherent viscous force and surface tension of the sodium alginate solution and makes the drug-containing polymer solution disperse into droplets of a certain size which are ejected to the curing solution and crosslinked quickly into calcium alginate microspheres (micro-gel beads). In order to prevent the water-soluble drug from releasing too early, the micro-gel bead is coated with the gelatin solution in the present invention; and in order to prevent the releasing (leaking) of the water-soluble drug from microspheres during the preservation period, the present invention employs a vegetable oil (or liquid paraffin) for preservation, which forming a water-in-oil system, so that loss of the drug before application can be avoided; the present invention employs the technology of high voltage electrostatic preparing sphere (capsule) so that organic solvents can be avoided, which helps to improve stability of the drug, and the particle size of the microsphere (capsule) can be adjusted by adjustment of voltage, the operation is simple and convenient, and the operation condition is mild, the toxic organic solvents and glutaraldehyde used in the prior art can be avoided, and the product of the present invention is environmentally friendly.

The present invention prepares microspheres in the presence of the divalent metal cation (calcium or barium ion) by using sodium alginate as a drug carrier crosslinking agent, the anti-tuberculosis drug of moxifloxacin as a drug active ingredient, and albumin as an adsorbent to link moxifloxacin and sodium alginate, and then the microspheres are coated with gelatin, which resolves the problem of too fast releasing of the water-soluble drug; in terms of preservation, autoclaved vegetable oil or liquid paraffin is used to preserve the wet gel drug microspheres so that moxifloxacin is not released when it is not used. The present invention changes the dosage form and administration route of the moxifloxacin anti-tuberculosis drug so as to achieve effects of efficient, low toxicity, and achieve safe and effective clinical application.

In the present invention, the anti-tuberculosis drug of moxifloxacin and the adsorbent (human serum albumin or bovine serum albumin) are grinded and dissolved, and mixed in proportion, before combined together by adsorption, and then crosslinked by with the sodium alginate carrier; and the anti-tuberculosis drug of moxifloxacin is wrapped in the microspheres by the high voltage electrostatic multi-head microsphere generating device in the presence of the divalent metal cation (calcium or barium ion); in order to prevent the anti-tuberculosis drug of moxifloxacin from releasing to the preservation solution, the microsphere is further coated with gelatin which forms a thin membrane around the microsphere, and then put into the autoclaved vegetable oil or liquid paraffin to preserve wet gel drug microspheres, so that the sodium alginate microsphere vascular targeting embolic agent containing moxifloxacin is prepared.

The present invention further relates to a vascular targeted embolic agent containing the above-mentioned sodium alginate crosslinked moxifloxacin sustained-release microsphere.

The present invention further relates to a use of the above-mentioned sodium alginate crosslinked moxifloxacin sustained-release microsphere in preparing a vascular targeted embolic agent. Said vascular targeted embolic agent may be used for treating tuberculosis, for example, used for treating pulmonary tuberculosis, mass hemoptysis of pulmonary tuberculosis or pulmonary tuberculosis cavity through interventional embolization; used for treating renal tuberculosis, thyroid tuberculosis, cervical lymph node tuberculosis, pericardial tuberculosis, chest wall tuberculosis and/or pleural tuberculosis; and used for treating fallopian tube tuberculosis, endometrium tuberculosis, testis tuberculosis or epididymis tuberculosis.

BENEFICIAL EFFECTS

The present invention has the following advantages:
1. a high voltage electrostatic multi-head microsphere generating device produced industrially is selected, so that the drug microsphere vascular targeted embolic agent suitable for different clinical uses with controllable size can be produced;
2. a natural polymer material, with good biocompatibility, i.e. sodium alginate is select as a drug carrier, so that a vascular targeted embolic agent containing biodegradable sustained-release drug microspheres can be obtained;
3. human serum albumin or bovine serum albumin is selected as an adsorbent, so that the anti-tuberculosis drug of moxifloxacin can be absorbed well.

The formulation of the present invention can not only improve local drug concentration greatly, decrease concentration of the drug in the circulation system, reduce toxicity of the drug to normal tissues, but also facilitate application of the drug greatly, reduce courses of treatment, shorten time for treatment, and reduce drug complications, treatment costs for patient and drug tolerance. In the treatment with the formulation of the present invention, the method of interventional radiology or bronchoscopic intervention is employed to perform target organ artery angiography, then embolic microspheres are chosen after the diameter of the embolic microspheres are determined according to the findings shown in angiography, and treatment of embolizing the target organ is performed with the chosen embolic microsphere, especially embolizing the peripheral small artery blood vessel of the target organ. Treatment of embolizing the peripheral small artery blood vessel may be considered for the following patients with pulmonary tuberculosis or following conditions: (1) patients subjected to failure in initial treatment and retreatment by adoping anti-tuberculosis therapy whose smear test shows tuberculosis-positive after the course of retreatment and sputum culture shows that *Mycobacterium tuberculosis* is resistant to two or more HR anti-tuberculosis drugs, i.e., multiple-drug resistant; (2) patients with the following symptoms: there is a single thin-wall or caseous cavity with tuberculosis bacilli in the sputum being persistently positive, and no apparently active lesion is around the cavity or the lesion has been stable; (3) patients with single fiber cavity of pulmonary tuberculosis and no negative conversion of sputum bacillus occurring after long time of treatment; (4) bronchial tuberculosis patients with sputum bacilli being persistently positive after long time of treatment; (5) interventional embolization treatment for mass hemoptysis of pulmonary tuberculosis; (6) intervention treatment for tuberculosises other than pulmonary tuberculosis, such as, renal tuberculosis, thyroid tuberculosis, cervical lymph node tuberculosis, pericardial tuberculosis, chest wall tuberculosis, pleural tuberculosis and genital tuberculosis (fallopian tube tuberculosis, endometrium tuberculosis, testis tuberculosis, epididymis tuberculosis), or the like.

When the formulation of the present invention is used, a micro-catheter is preferably used to perform superselective embolization, the sterile operation is employed, and injection is performed slowly as required or slowly performed multiple times under fluoroscopy through the catheter until the flow rate of the contrast agent decreases significantly, and embolization is completed. Further artery angiography is performed to evaluate embolization effect. During application, if the sodium alginate microsphere vascular embolic agent containing the moxifloxacin anti-tuberculosis drug is powdered particles, dry spheres preserved in a sealed container are firstly dissolved in physiological saline to reconstituted to wet spheres, then an appropriate amount of contrast agent or diluted contrast agent is added and the mixture is mixed uniformly to make the microspheres fully suspended in the contrast agent, then under monitoring by an imaging equipment, the mixture is injected into the blood vessel at the lesion site slowly or injected slowly multiple times by catheter, so as to achieve a super-selective embolization until the flow rate of the contrast agent decreases obviously, and embolization is completed. Further artery angiography is performed and embolization effect is determined.

The outstanding advantages of the present invention are as follows: human serum albumin or bovine serum albumin used as an adsorbent are safe and effective, which successfully resolves the problem that moxifloxacin cannot dissolve in water or organic solvents completely, the difficult problem that when the combination of moxifloxacin and the albumin is mixed and crosslinked with water-soluble sodium alginate solution, the mixture is unsinkable, and the problem that drug microspheres cannot be formed when moxifloxacin reacts with other reagents and is wrapped under the action of positive and negative electric fields; size of anti-tuberculosis drug microspheres prepared is ideal and controllable, and the microsphere vascular embolic agent prepared has characteristics of high drug loading, long retention time in the body and high bioavailability, adjustable drug releasing rate, being capable of achieving targeted delivery of the drug, and target specificity, and can be used to treat pulmonary tuberculosis, mass hemoptysis of pulmonary tuberculosis, pulmonary tuberculosis cavity, renal tuberculosis, thyroid tuberculosis, cervical lymph node tuberculosis, genital tuberculosis (fallopian tube tuberculosis, endometrium tuberculosis, testis tuberculosis, epididymis tuberculosis), pericardial tuberculosis, chest wall tuberculosis, pleural tuberculosis and other tuberculosises in the body through interventional embolization.

DETAILED DESCRIPTION OF THE PREFERRED EMBODIMENTS

The present invention will be further illustrated in combination with embodiments, and it should be understood that the preferred embodiments described herein are only used to illustrate and explain the present invention, rather than limit the present invention.

Example 1

Preparation of Sodium Alginate Crosslinked Moxifloxacin Anti-Tuberculosis Microsphere Vascular Embolic Agent 1. Treatment of glassware:

The cleaned glassware was dried out in the air and then placed and baked in the high-temperature oven (for sterilization and depyrogenation) to be used.

2. Selection of Microsphere Preparing Device:

A high voltage electrostatic multi-head microsphere generating device, which can controllably prepare spheres with uniform size, is simple and convenient to operate, has high output, and easily implements mass production, was selected.

3. Method for Preparing Various Reagents:

(1) Preparation of sodium alginate solution:

8 g of sodium alginate was weighed and placed in a glassware, then 500 ml of physiological saline or water for injection was added into the glassware while stirring, magnetical stirring was performed until all the sodium alginate was dissolved to obtain a sodium alginate solution;

(2) Preparation of adsorbent:

Human serum albumin (or bovine serum albumin) was dissolved with water for injection at a ratio of 0.1~10% (mass-volume percentage) to obtain an albumin solution, i.e., an adsorbent;

(3) Preparation of moxifloxacin solution:

12 g of commercially available moxifloxacin was weighed, placed in a glassware, and dissolved with 50 ml of the human serum albumin or bovine serum albumin solution of 0.1~10% (mass-volume percentage) by stirring to obtain a moxifloxacin solution;

(4) Preparation of gelatin strengthening solution:

30 g of gelatin was placed in a glassware, 500 ml of physiological saline or water for injection was added into the glassware while stirring, magnetical stirring was performed until all the gelatin were dissolved to obtain a gelatin strengthening solution;

(5) Preparation of curing solution containing anhydrous ethanol:

200 g of calcium chloride or barium chloride or calcium lactate was weighed and placed in a glassware, 4,000 ml of water for injection was added into the glassware while stirring, magnetical stirring was performed until the calcium compound was dissolved, and then 1,000 ml of anhydrous ethanol was added to obtain a curing solution containing anhydrous ethanol;

(6) Preparation of preservation solution:

The purchased soybean oil (or tea oil, corn oil, peanut oil, rapeseed oil, cottonseed oil or other oils for injection) or liquid paraffin for injection was used as a preservation solution;

(7) Preparation of mixed solution:

The sodium alginate solution and the moxifloxacin solution prepared above were mixed and stirred uniformly to obtain a mixed solution.

4. Preparation of microspheres:

The above-obtained mixed solution was aspirated by a sterile syringe, and dripped into the above-obtained curing solution through the high voltage electrostatic multi-head microsphere liquid drop generating device, microspheres or micro-gel beads with different particle size ranges were prepared as required, and the resulting sodium alginate crosslinked moxifloxacin microspheres or micro-gel beads sank into the bottom of the container.

The high voltage electrostatic multi-head microsphere generating device comprises: a high voltage electrostatic generating device, propulsion pump, ejecting head, sterile container, positive and negative electrodes, sterile syringes of various models, and a lifting device. The high voltage electrostatic multi-head generating device has two electrodes of positive and negative electrodes in every group, the propulsion pump is connected to the sterile syringe and the ejecting head, the positive electrode is connected to the ejecting head, the negative electrode is connected to the stainless steel wire immersed in the curing solution, and the stainless steel wire is connected to the sterile container, and the lifting device for adjusting distance is under the stainless steel wire and the sterile container.

Particle sizes of said microspheres or micro-gel beads preserved in the preservation solution are as follows: 50~100 μm, 50~150 μm, 50~200 μm, 100~300 μm, 150~450 μm, 300~500 μm, 500~700 μm, 700~900 μm or 900~1,250 μm. After the upper layer of the solution in the above-mentioned container was decanted, the microspheres or micro-gel beads were washed with physiological saline for immediate use.

The upper layer solution of the above-obtained microspheres was decanted, and the resulting sodium alginate microspheres containing the moxifloxacin anti-tuberculosis drug was dried (the method of freeze drying or oven drying was used to prepare dry spheres) to obtain powdered particles; the particle sizes of the powdered particles are in the range of 10~50 μm, 25~50 μm, 50~100 μm, 100~350 μm, 300~550 μm or 500~750 μm; the powdered particles were sealed for preservation, and before use, the powdered particles were soaked with physiological saline for a few minutes to be reconstituted to wet spheres.

Patients with pulmonary tuberculosis were treated by the method of interventional radiology or bronchoscopic intervention, wherein a catheter was inserted into the opening of target organ segment, a guide wire was introduced under monitoring by X-ray, and artery angiography was performed when the catheter was embedded into the blood vessel lumen. According to the findings shown in angiography, continuous photographs confirmed that the front end of the catheter was fixed, the guide wire was exited, and the catheter was retained, and the appropriate particle size range was selected for the above-mentioned sodium alginate crosslinked moxifloxacin microspheres; the sodium alginate crosslinked moxifloxacin microspheres (wet spheres) were washed with physiological saline for three times, generally 500~700 μm microspheres can produce better effect, then an appropriate amount of contrast agent was added and mixed uniformly, the mixture was slowly injected into the lesion site via the catheter under fluoroscopy until the flow rate of the contrast agent decreased significantly, and then embolization was completed. Further artery angiography was performed to evaluate embolization effect.

Example 2

Preparation of Sodium Alginate Crosslinked Moxifloxacin Anti-Tuberculosis Microsphere Vascular Embolic Agent 1. Treatment of glassware:

The cleaned glassware was dried out in the air and then placed and baked in the high-temperature oven (for sterilization and depyrogenation) to be used.

2. Selection of microsphere preparing device:

A high voltage electrostatic multi-head microsphere generating device, which can controllably prepare spheres with uniform size, is simple and convenient to operate, has high output, and easily implements mass production, was selected.

3. Method for preparing various reagents:

(1) Preparation of sodium alginate solution:

10 g of sodium alginate was weighed and placed in a glassware, then 500 ml of physiological saline or water for injection was added into the glassware while stirring, magnetical stirring was performed until all the sodium alginate was dissolved to obtain a sodium alginate solution;

(2) Preparation of adsorbent:

Human serum albumin (or bovine serum albumin) was dissolved with water for injection at a ratio of 0.1~10% (mass-volume percentage) to obtain an adsorbent, i.e., an albumin solution;

(3) Preparation of moxifloxacin anti-tuberculosis drug solution:

14 g of commercially available moxifloxacin was weighed, placed in a glassware, and dissolved with 50 ml of the human serum albumin or bovine serum albumin solution of 0.1~10% (mass-volume percentage) by stirring to obtain a moxifloxacin anti-tuberculosis drug solution;

(4) Preparation of gelatin strengthening solution:

26 g of gelatin was placed in a glassware, 500 ml of physiological saline or water for injection was added into the glassware while stirring, magnetical stirring was performed until all the gelatin was dissolved to obtain a gelatin strengthening solution;

(5) Preparation of curing solution containing anhydrous ethanol:

200 g of calcium chloride or barium chloride or calcium lactate was weighed and placed in a glassware, and 4,000 ml of water for injection was added into the glassware while stirring, magnetical stirring was performed until the calcium compound was dissolved, and then 1,000 ml of anhydrous ethanol was added to obtain a curing solution containing anhydrous ethanol;

(6) Preparation of preservation solution:

The purchased soybean oil (or tea oil, corn oil, peanut oil, rapeseed oil, cottonseed oil or other oils for injection) or liquid paraffin for injection was used as a preservation solution;

(7) Preparation of mixed solution:

The sodium alginate solution and moxifloxacin anti-tuberculosis drug solution prepared above were mixed and stirred uniformly to obtain a mixed solution.

4. Preparation of microspheres:

The above-obtained mixed solution was aspirated by a sterile syringe, and dripped into the above-obtained curing solution through the high voltage electrostatic multi-head microsphere liquid drop generating device, microspheres or micro-gel beads within different particle size ranges were prepared as required, and the resulting sodium alginate crosslinked moxifloxacin microspheres or micro-gel beads sank into the bottom of the container.

The high voltage electrostatic multi-head microsphere generating device comprises: a high voltage electrostatic generating device, propulsion pump, ejecting head, sterile container, positive and negative electrodes, sterile syringes of various models, and a lifting device. The high voltage electrostatic multi-head generating device has two electrodes of positive and negative electrodes in every group, the propulsion pump is connected to the sterile syringe and the ejecting head, the positive electrode is connected to the ejecting head, the negative electrode is connected to the stainless steel wire immersed in the curing solution, and the stainless steel wire is connected to the sterile container, and the lifting device for adjusting distance is under the stainless steel wire and the sterile container.

Particle sizes of said microspheres or micro-gel beads preserved in the preservation solution are as follows: 50~100 μm, 50~150 μm, 50~200 μm, 100~300 μm, 150~450 μm, 300~500 μm, 500~700 μm, 700~900 μm or 900~1,250 μm. After the upper layer of the solution in the above-mentioned container was decanted, the microspheres or micro-gel beads were washed with physiological saline for immediate use.

The upper layer solution of the above-obtained microspheres was decanted, and the resulting sodium alginate microspheres containing the moxifloxacin anti-tuberculosis drug was dried (the method of freeze drying or oven drying was used to prepare dry spheres) to obtain powdered particles; the particle sizes of the powdered particles are in the range of 10~50 μm, 25~50 μm or 50~100 μm; 100~350 μm, 300~550 μm or 500~750 μm; the powdered particles were sealed for preservation, and before use, the powdered particles were soaked with physiological saline for a few minutes to be reconstituted to wet spheres.

Patients with pulmonary tuberculosis cavity were treated by the method of interventional radiology or bronchoscopic intervention, wherein a catheter was inserted into the opening of target organ segment, a guide wire was introduced under monitoring by X-ray, and artery angiography was performed when the catheter was embedded into the blood vessel lumen. According to the findings shown in angiography, continuous photographs confirmed that the front end of the catheter was fixed, the guide wire was exited, and the catheter was retained, and the appropriate particle size range was selected for the above-mentioned sodium alginate crosslinked moxifloxacin microspheres; the sodium alginate crosslinked moxifloxacin microspheres (wet spheres) were washed with physiological saline for three times, generally 700~900 μm microspheres can produce better effect, then an appropriate amount of contrast agent was added and mixed uniformly, the mixture was slowly injected into the lesion site via the catheter under fluoroscopy until the flow rate of the contrast agent decreased significantly, and then embolization was completed. Further artery angiography was performed to evaluate embolization effect.

Results of clinical trials show that the drug microspheres of the present invention can be used for embolizing peripheral small artery blood vessel, after embolization, no pressure difference is generated between two ends of potential collateral circulation blood vessels, it is not easy to form a secondary collateral circulation, and the drug can be delivered to the target organs and target cells; when applied, the drug can be highly concentrated in the lesion site, and only minimal amount of drug exist in the normal site, the therapeutic effect is improved and the systemic toxic and side effect is reduced, primary blood supply to sites of tuberculosis is effectively cut off, the flushing action of blood flow on the drug is blocked, and the duration of action of the drug is extended, so that the therapeutic purpose can be achieved.

Example 3

Preparation of Sodium Alginate Crosslinked Moxifloxacin Anti-Tuberculosis Microsphere Vascular Embolic Agent 1. Treatment of glassware:
The cleaned glassware was dried out in the air and then placed and baked in the high-temperature oven (for sterilization and depyrogenation) to be used.

2. Selection of microsphere preparing device:
A high voltage electrostatic multi-head microsphere generating device, which can controllably prepare spheres with uniform size, is simple and convenient to operate, has high output, and easily implements mass production, was selected.

3. Method for preparing various reagents:
(1) Preparation of sodium alginate solution:
15 g of sodium alginate was weighed and placed in a glassware, then 500 ml of physiological saline or water for injection was added into the glassware while stirring, magnetical stirring was performed until all the sodium alginate was dissolved to obtain a sodium alginate solution;

(2) Preparation of adsorbent:
Human serum albumin (or bovine serum albumin) was dissolved with water for injection at a ratio of 0.1~10% (mass-volume percentage) to obtain an adsorbent, i.e., an albumin solution;

(3) Preparation of moxifloxacin anti-tuberculosis drug solution:
10 g of commercially available moxifloxacin was weighed, placed in a glassware, and dissolved with 50 ml of the human serum albumin or bovine serum albumin solution of 0.1~10% (mass-volume percentage) by stirring to obtain a moxifloxacin anti-tuberculosis drug solution;

(4) Preparation of gelatin strengthening solution:
20 g of gelatin was placed in a glassware, 500 ml of physiological saline or water for injection was added into the glassware while stirring, magnetical stirring was performed until all the gelatin was dissolved to obtain a gelatin strengthening solution;

(5) Preparation of curing solution containing anhydrous ethanol:
200 g of calcium chloride or barium chloride or calcium lactate was weighed and placed in a glassware, and 4,000 ml of water for injection was added into the glassware while stirring, magnetical stirring was performed until the calcium compound was dissolved, and then 1,000 ml of anhydrous ethanol was added to obtain a curing solution containing anhydrous ethanol;

(6) Preparation of preservation solution:
The purchased soybean oil (or tea oil, corn oil, peanut oil, rapeseed oil, cottonseed oil or other oils for injection) or liquid paraffin for injection was used as a preservation solution;

(7) Preparation of mixed solution:
The sodium alginate solution and moxifloxacin anti-tuberculosis drug solution prepared above were mixed and stirred uniformly to obtain a mixed solution.

4. Preparation of microspheres
The above-obtained mixed solution was aspirated by a sterile syringe, and dripped into the above-obtained curing solution through the high voltage electrostatic multi-head microsphere liquid drop generating device, microspheres or micro-gel beads within different particle size ranges were prepared as required, and the resulting sodium alginate crosslinked moxifloxacin microspheres or micro-gel beads sank into the bottom of the container.

The high voltage electrostatic multi-head microsphere generating device comprises: a high voltage electrostatic generating device, propulsion pump, ejecting head, sterile container, positive and negative electrodes, sterile syringes of various models, and a lifting device. The high voltage electrostatic multi-head generating device has two electrodes of positive and negative electrodes in every group, the propulsion pump is connected to the sterile syringe and the ejecting head, the positive electrode is connected to the ejecting head, the negative electrode is connected to the stainless steel wire immersed in the curing solution, and the stainless steel wire is connected to the sterile container, and the lifting device for adjusting distance is under the stainless steel wire and the sterile container.

Particle sizes of said microspheres or micro-gel beads preserved in the preservation solution are as follows: 50~100 μm, 50~150 μm, 50~200 μm, 100~300 μm, 150~450 μm, 300~500 μm, 500~700 μm, 700~900 μm or 900~1,250 μm. After the upper layer of the solution in the above-mentioned container was decanted, the microspheres or micro-gel beads were washed with physiological saline for immediate use.

The upper layer solution of the above-obtained microspheres was decanted, and the resulting sodium alginate microspheres containing the moxifloxacin anti-tuberculosis drug was dried (the method of freeze drying or oven drying was used to prepare dry spheres) to obtain powdered particles; the particle sizes of the powdered particles are in the range of 10~50 μm, 25~50 μm or 50~100 μm; 100~350 μm, 300~550 μm or 500~750 μm; the powdered particles were sealed for preservation, and before use, the powdered particles were soaked with physiological saline for a few minutes to be reconstituted to wet spheres.

Patients with mass hemoptysis of pulmonary tuberculosis were treated by the method of interventional radiology or bronchoscopic intervention, wherein a catheter was inserted into the feeding artery in the target organ, and artery angiography was performed. According to the findings shown in angiography, the appropriate particle size range was selected for the above-mentioned sodium alginate microspheres containing moxifloxacin. The sodium alginate crosslinked moxifloxacin microspheres (wet spheres) were washed with physiological saline for three times, generally 500~700 μm or 700~900 μm microspheres can produce better effect, then an appropriate amount of contrast agent was added and mixed uniformly, the mixture was slowly injected into the lesion site via the catheter under fluoroscopy until the flow rate of the contrast agent decreased significantly, and then embolization was completed. Further artery angiography was performed to evaluate embolization effect.

Results of clinical trials show that the solvent used in the present invention is effective and safe, when the catheter is inserted into the target blood vessel, microspheres containing the drug is mixed with the contrast agent by a syringe after angiography, and when the mixture of the microspheres and contrast agent is slowly injected into the catheter, no aggregation occurs and no catheters is blocked. Particle sizes of said drug microspheres are appropriate (generally 500~700 μm or 700~900 μm microspheres can produce better effect), and the drug microspheres have advantages such as, having good biocompatibility, being nontoxic and harmless to human bodies, and non-immunogenic, having affinity with the drug carried, low drug toxic and side effects, high drug concentration and high utilization.

Example 4

Preparation of Sodium Alginate Crosslinked Moxifloxacin Anti-Tuberculosis Microsphere Vascular Embolic Agent 1. Treatment of glassware:
    The cleaned glassware was dried out in the air, and then placed and baked in the high-temperature oven (for sterilization and depyrogenation) to be used.

2. Selection of microsphere preparing device:
    A high voltage electrostatic multi-head microsphere generating device, which can controllably prepare spheres with uniform size, is simple and convenient to operate, has high output, and easily implements mass production, was selected.
3. Method for preparing various reagents:
    (1) Preparation of sodium alginate solution:
        20 g of sodium alginate was weighed and placed in a glassware, then 500 ml of physiological saline or water for injection was added into the glassware while stirring, magnetical stirring was performed until all the sodium alginate was dissolved to obtain a sodium alginate solution;
    (2) Preparation of adsorbent:
        Human serum albumin (or bovine serum albumin) was dissolved with water for injection at a ratio of 0.1~10% (mass-volume percentage) to obtain an adsorbent, i.e., an albumin solution;
    (3) Preparation of moxifloxacin anti-tuberculosis drug solution:
        22 g of commercially available moxifloxacin was weighed, placed in a glassware, and dissolved with 50 ml of the human serum albumin or bovine serum albumin solution of 0.1~10% (mass-volume percentage) by stirring to obtain a moxifloxacin anti-tuberculosis drug solution;
    (4) Preparation of gelatin strengthening solution:
        22 g of gelatin was placed in a glassware, 500 ml of physiological saline or water for injection was added into the glassware while stirring, magnetical stirring was performed until all the gelatin was dissolved to obtain a gelatin strengthening solution;
    (5) Preparation of curing solution containing anhydrous ethanol:
        200 g of calcium chloride or barium chloride or calcium lactate was weighed and placed in a glassware, and 4,000 ml of water for injection was added into the glassware while stirring, magnetical stirring was performed until the calcium compound was dissolved, and then 1,000 ml of anhydrous ethanol was added to obtain a curing solution containing anhydrous ethanol;
    (6) Preparation of preservation solution:
        The purchased soybean oil (or tea oil, corn oil, peanut oil, rapeseed oil, cottonseed oil or other oils for injection) or liquid paraffin for injection was used as a preservation solution;
    (7) Preparation of mixed solution:
        The sodium alginate solution and moxifloxacin anti-tuberculosis drug solution prepared above were mixed and stirred uniformly to obtain a mixed solution.
4. Preparation of microspheres:
    The above-obtained mixed solution was aspirated by a sterile syringe, and dripped into the above-obtained curing solution through the high voltage electrostatic multi-head microsphere liquid drop generating device, microspheres or micro-gel beads within different particle size ranges were prepared as required, and the resulting sodium alginate crosslinked moxifloxacin microspheres or micro-gel beads sank into the bottom of the container.

The high voltage electrostatic multi-head microsphere generating device comprises: a high voltage electrostatic generating device, propulsion pump, ejecting head, sterile container, positive and negative electrodes, sterile syringes of various models, and a lifting device. The high voltage electrostatic multi-head generating device has two electrodes of positive and negative electrodes in every group, the propulsion pump is connected to the sterile syringe and the ejecting head, the positive electrode is connected to the ejecting head, the negative electrode is connected to the stainless steel wire immersed in the curing solution, and the stainless steel wire is connected to the sterile container, and the lifting device for adjusting distance is under the stainless steel wire and the sterile container.

Particle sizes of said microspheres or micro-gel beads preserved in the preservation solution are as follows: 50~100 μm, 50~150 μm, 50~200 μm, 100~300 μm, 150~450 μm, 300~500 μm, 500~700 μm, 700~900 μm or 900~1,250 μm. After the upper layer of the solution in the above-mentioned container was decanted, the microspheres or micro-gel beads were washed with physiological saline for immediate use.

The upper layer solution of the above-obtained microspheres obtained above was decanted, and the resulting sodium alginate microspheres containing the moxifloxacin anti-tuberculosis drug was dried (the method of freeze drying or oven drying was used to prepare dry spheres) to obtain powdered particles; the particle sizes of the powdered particles are in the range of 10~50 μm, 25~50 μm or 50~100 μm; 100~350 μm, 300~550 μm or 500~750 μm; the powdered particles were sealed for preservation, and before use, the powdered particles were soaked with physiological saline for a few minutes to be reconstituted to wet spheres.

The method of interventional radiology or bronchoscopic intervention is used to treat patients with tuberculosis other than pulmonary tuberculosis, such as renal tuberculosis, thyroid tuberculosis, cervical lymph node tuberculosis, genital tuberculosis (fallopian tube tuberculosis, endometrium tuberculosis, testis tuberculosis, epididymis tuberculosis), pericardial tuberculosis, chest wall tuberculosis, pleural tuberculosis and other tuberculosises in the body.

A catheter was inserted into the feeding artery in the target organ, and artery angiography was performed. According to the findings shown in angiography, the appropriate particle size range was selected for the above-mentioned sodium alginate microspheres containing moxifloxacin. The sodium alginate crosslinked moxifloxacin microspheres (wet spheres) were washed with physiological saline for three times, generally 300~500 μm microspheres can produce better effect, then an appropriate amount of contrast agent was added and mixed uniformly, the mixture was slowly injected into the lesion site via the catheter under fluoroscopy until the flow rate of the contrast agent decreased significantly, and then embolization was completed. Further artery angiography was performed to evaluate embolization effect. Results of clinical trials show that the solvent used in the present invention is effective and safe, local concentration of the drug is increased while the total amount of drug is decreased, the incidence of systemic toxic and side effect is reduced; when the biodegradable microspheres containing the drug is implanted into the tuberculosis, the release rate of the drug can approach zero-order release rate, stable drug concentration can be maintained, no burst releasing effect is produced, and it is not necessary to remove microspheres by operation.

Those skilled in the art can understand that the description hereinbefore are only preferred embodiments of the present invention and not intended to limit the present invention. Although the present invention is illustrated in detail with reference to the aforementioned embodiments, those skilled in the art can still modify the technical solutions of the foregoing embodiments or perform equivalent substitution on part of the technical features. Any modifications, equivalent substitutions, improvements and the like made within the spirit and principle of the present invention shall be included within the protection scope of the present invention.

The invention claimed is:

1. A sodium alginate crosslinked moxifloxacin sustained-release microsphere, comprising: a drug carrier, adsorbent, anti-tuberculosis drug active ingredient, strengthening agent and curing agent, wherein the carrier is sodium alginate, the adsorbent is human serum albumin or bovine serum albumin, the anti-tuberculosis drug active ingredient is water-insoluble moxifloxacin, the strengthening agent is gelatin or hyaluronic acid, and the curing agent is a salt of a divalent metal cation, wherein the water-insoluble moxifloxacin is dissolved in an aqueous solution comprising the adsorbent before preparing the microsphere.

2. The sustained-release microsphere according to claim 1, wherein when the microsphere is preserved in vegetable oil or liquid paraffin as a preservation solution, the particle size of the microsphere is in the range of 50-100 μm, 50-150 μm, 50-200 μm, 100-300 μm, 150-450 μm, 300-500 μm, 500-700 μm, 700-900 μm or 900-1,250 μm.

3. The sustained-release microsphere according to claim 1, wherein the microsphere is a dry powdered particle with particle size in the range of 10-50 μm, 25-50 μm, 50-100 μm, 100-350 μm, 300-550 μm or 500-750 μm.

4. The sustained-release microsphere according to claim 1, wherein the weight ratio of sodium alginate and moxifloxacin is 1-75:0.25-12.5.

5. A method for preparing the sustained-release microsphere according to claim 1, comprising the following steps:
1) dissolving sodium alginate with physiological saline or water for injection based on mass-volume percentage of 0.5-15% to obtain a sodium alginate solution as a carrier solution;
2) dissolving human serum albumin or bovine serum albumin with water for injection based on mass-volume percentage of 0.1-10% to obtain a albumin solution as an adsorbent;
3) grinding, stirring, dissolving and adsorbing moxifloxacin with the adsorbent prepared in step 2) to obtain a moxifloxacin solution as a drug solution, wherein moxifloxacin and the adsorbent are added in an amount of mass-volume percentage of 1.6-4%;
4) preparing an aqueous solution of 1-15% by mass-volume with a salt of divalent metal cation to obtain a curing solution;
5) adding anhydrous ethanol and water for injection into the resulting curing solution, wherein the volume ratio of the curing solution, anhydrous ethanol and water for injection is 2:1:2, so that a curing solution containing anhydrous ethanol is obtained;
6) dissolving gelatin or hyaluronic acid with water for injection to obtain a gelatin or hyaluronic acid solution of 0.1-10% by mass-volume as a strengthening solution;
7) pooling the drug solution and the carrier solution at a volume ratio of 1:1-30, and magnetically stirring the solution uniformly to obtain a preparing solution;
8) spraying the preparing solution by a high voltage electrostatic multi-head microsphere generating device to obtain droplets which are then dispersed in the curing solution containing anhydrous ethanol, and removing supernatant when precipitation is completed, to obtain sodium alginate crosslinked microspheres containing moxifloxacin; and
9) adding and stirring the sodium alginate crosslinked microspheres containing moxifloxacin into the strengthening solution, and discarding supernatant to obtain sodium alginate crosslinked moxifloxacin sustained-release microspheres.

6. The method according to claim 5, wherein the sustained-release microspheres containing moxifloxacin obtained in step 9) are preserved in vegetable oil or liquid paraffin oil.

7. The method according to claim 5, wherein the preparing of the aqueous solution in step 4) comprises preparing the aqueous solution of 1-15% by mass-volume with a divalent calcium or barium salt to obtain the curing solution.

8. The method according to claim 7, wherein the calcium salt is calcium chloride or calcium lactate, and the barium salt is barium chloride.

9. The method according to claim 5, wherein the high voltage electrostatic multi-head microsphere generating device used in step 8) comprises: a high voltage electrostatic generating device, propulsion pump, an ejecting head, a sterile container, a positive electrode, a negative electrode, a sterile syringe, and a lifting device, wherein the high voltage electrostatic generating device is provided with the positive and negative electrodes, the propulsion pump is connected to the sterile syringe and the ejecting head, the positive electrode is connected to the ejecting head, the negative electrode is connected to a stainless steel wire immersed in the curing solution containing anhydrous ethanol, the stainless steel wire is connected to the sterile container, and the lifting device for adjusting distance is under the stainless steel wire and the sterile container.

10. A vascular targeted embolic agent containing the sustained-release microsphere according to claim 1.

11. A method for treating a subject suffering from tuberculosis, wherein the method comprises administering to the subject an effective amount of vascular targeted embolic agent according to claim 10.

12. The method according to claim 11, wherein the tuberculosis is selected from renal tuberculosis, thyroid tuberculosis, cervical lymph node tuberculosis, pericardial tuberculosis, chest wall tuberculosis and pleural tuberculosis.

13. The method according to claim 11, wherein the tuberculosis is selected from fallopian tube tuberculosis, endometrium tuberculosis, testis tuberculosis and epididymis tuberculosis.

14. The method according to claim 11, wherein the tuberculosis is selected from pulmonary tuberculosis, mass hemoptysis of pulmonary tuberculosis, or pulmonary tuberculosis cavity.

15. The sustained-release microsphere according to claim 1, wherein the curing agent is a divalent calcium or barium salt.

16. The method according to claim 6, wherein the high voltage electrostatic multi-head microsphere generating device used in step 8) comprises: a high voltage electrostatic generating device, a propulsion pump, an ejecting head, a sterile container, a positive electrode, a negative electrode, a sterile syringe, and a lifting device, wherein the high voltage electrostatic generating device is provided with the positive and negative electrodes, the propulsion pump, is connected to the sterile syringe and the ejecting head, the positive electrode is connected to the ejecting head, the negative electrode is connected to a stainless steel wire immersed in the curing solution containing anhydrous ethanol, the stainless steel wire is connected to the sterile container, and the lifting device for adjusting distance is under the stainless steel wire and the sterile container.

17. The method according to claim 8, wherein the high voltage electrostatic multi-head microsphere generating device used in step 8) comprises: a high voltage electrostatic generating device, a propulsion pump, an ejecting head, a sterile container, a positive electrode, a negative electrode, a sterile syringe, and a lifting device, wherein the high voltage electrostatic generating device is provided with the positive and negative electrodes, the propulsion pump is connected to the sterile syringe and the ejecting head, the positive electrode is connected to the ejecting head, the negative electrode is connected to a stainless steel wire immersed in the curing solution containing anhydrous ethanol, the stainless steel wire is connected to the sterile container, and the lifting device for adjusting distance is under the stainless steel wire and the sterile container.

18. A vascular targeted embolic agent containing the sustained-release microsphere according to claim 2.

19. A vascular targeted embolic agent containing the sustained-release microsphere according to claim 3.

20. A vascular targeted embolic agent containing the sustained-release microsphere according to claim 4.

* * * * *